United States Patent [19]
Hooven

[11] Patent Number: 6,036,681
[45] Date of Patent: Mar. 14, 2000

[54] APPARATUS AND METHOD FOR MORSELATING AND REMOVING TISSUE FROM A PATIENT

[75] Inventor: Michael D. Hooven, Cincinnati, Ohio

[73] Assignee: Enable Medical Corporation, West Chester, Ohio

[21] Appl. No.: 08/924,805

[22] Filed: Sep. 5, 1997

Related U.S. Application Data

[62] Division of application No. 08/386,970, Feb. 10, 1995, Pat. No. 5,814,044.

[51] Int. Cl.⁷ .................................................. A61M 31/00
[52] U.S. Cl. ........................................... 604/506; 604/500
[58] Field of Search .................... 606/45–48, 50, 606/28, 127–128, 167, 180; 604/19–22, 28, 49, 48, 267, 280, 500, 506–507, 514

[56] References Cited

U.S. PATENT DOCUMENTS

| | | |
|---|---|---|
| 2,419,045 | 4/1947 | Whittaker . |
| 3,120,845 | 2/1964 | Horner . |
| 3,945,375 | 3/1976 | Banko . |
| 3,987,795 | 10/1976 | Morrison . |
| 3,990,453 | 11/1976 | Douvas et al. . |
| 4,016,881 | 4/1977 | Rioux . |
| 4,220,154 | 9/1980 | Semm . |
| 4,461,305 | 7/1984 | Cibley . |
| 4,483,338 | 11/1984 | Bloom et al. . |
| 4,674,499 | 6/1987 | Pao . |
| 4,682,596 | 7/1987 | Bales et al. . |
| 4,729,763 | 3/1988 | Henrie . |
| 4,931,047 | 6/1990 | Broadwin et al. . |
| 5,009,656 | 4/1991 | Reimels . |
| 5,015,227 | 5/1991 | Broadwin et al. . |
| 5,037,379 | 8/1991 | Clayman et al. . |
| 5,074,867 | 12/1991 | Wilk . |
| 5,084,045 | 1/1992 | Helenowski . |
| 5,133,360 | 7/1992 | Spears . |
| 5,133,713 | 7/1992 | Huang et al. . |
| 5,143,082 | 9/1992 | Kindberg et al. . |
| 5,160,334 | 11/1992 | Billings et al. . |
| 5,171,311 | 12/1992 | Rydell et al. . |
| 5,176,687 | 1/1993 | Hasson et al. . |

(List continued on next page.)

OTHER PUBLICATIONS

1. PCT International Search Report, Application No. PCT/US96/01547, filed Feb. 6, 1996 (claiming priority on U.S. application serial No. 08/386,970, filed Feb. 10, 1995, 1988.
2. Brochure: Cook® Tissue Morcellator™ and Lapsac™ .

*Primary Examiner*—Wynn Wood Coggins
*Assistant Examiner*—Jennifer R. Sadula
*Attorney, Agent, or Firm*—Cook, Alex, McFarron, Manzo, Cummings & Mehler, Ltd.

[57] ABSTRACT

A method for morselating and removing the morselated tissue through a small incision comprising in general inserting a tissue container into the body cavity of a patient through an incision, placing resected tissue in the vessel, inserting a morselator having a rotatable electrode thereon through the incision and into the vessel, morselating the tissue and removing the tissue from the containment vessel and the body. An apparatus for morselating and removing tissue through a small incision within the body cavity of a patient is also disclosed and may comprise a tissue container having an inner chamber for containing resected tissue, and a morselator having a proximal end and a distal end carrying an electrode wherein the distal end is insertable into the body cavity and containment vessel for morselating resected tissue.

14 Claims, 7 Drawing Sheets

U.S. PATENT DOCUMENTS

| | | |
|---|---|---|
| 5,186,714 | 2/1993 | Boudreault . |
| 5,190,542 | 3/1993 | Nakao et al. . |
| 5,197,968 | 3/1993 | Clement . |
| 5,201,730 | 4/1993 | Easley et al. . |
| 5,207,684 | 5/1993 | Nobles . |
| 5,207,697 | 5/1993 | Carusillo et al. . |
| 5,215,521 | 6/1993 | Cochran et al. . |
| 5,217,468 | 6/1993 | Clement . |
| 5,221,281 | 6/1993 | Klicek . |
| 5,234,439 | 8/1993 | Wilk et al. . |
| 5,254,117 | 10/1993 | Rigby et al. . |
| 5,273,524 | 12/1993 | Fox et al. . |
| 5,275,609 | 1/1994 | Pingleton et al. . |
| 5,277,696 | 1/1994 | Hagen . |
| 5,281,216 | 1/1994 | Klicek . |
| 5,282,799 | 2/1994 | Rydell . |
| 5,290,303 | 3/1994 | Pingleton et al. . |
| 5,304,124 | 4/1994 | Essig et al. . |
| 5,312,416 | 5/1994 | Spaeth et al. . |
| 5,320,627 | 6/1994 | Sorensen et al. . |
| 5,324,288 | 6/1994 | Billings et al. . |
| 5,324,300 | 6/1994 | Elias et al. . |
| 5,330,483 | 7/1994 | Heaven et al. . |
| 5,336,237 | 8/1994 | Chin et al. . |
| 5,346,497 | 9/1994 | Simon et al. . |
| 5,354,303 | 10/1994 | Spaeth et al. . |
| 5,387,196 | 2/1995 | Green et al. . |
| 5,409,487 | 4/1995 | Jalbert et al. . |
| 5,451,224 | 9/1995 | Goble et al. . |
| 5,464,404 | 11/1995 | Abela et al. . |
| 5,520,634 | 5/1996 | Fox et al. . |
| 5,542,916 | 8/1996 | Hirsh et al. . |
| 5,571,100 | 11/1996 | Goble et al. . |
| 5,573,534 | 11/1996 | Stone . |
| 5,688,269 | 11/1997 | Newton et al. . |

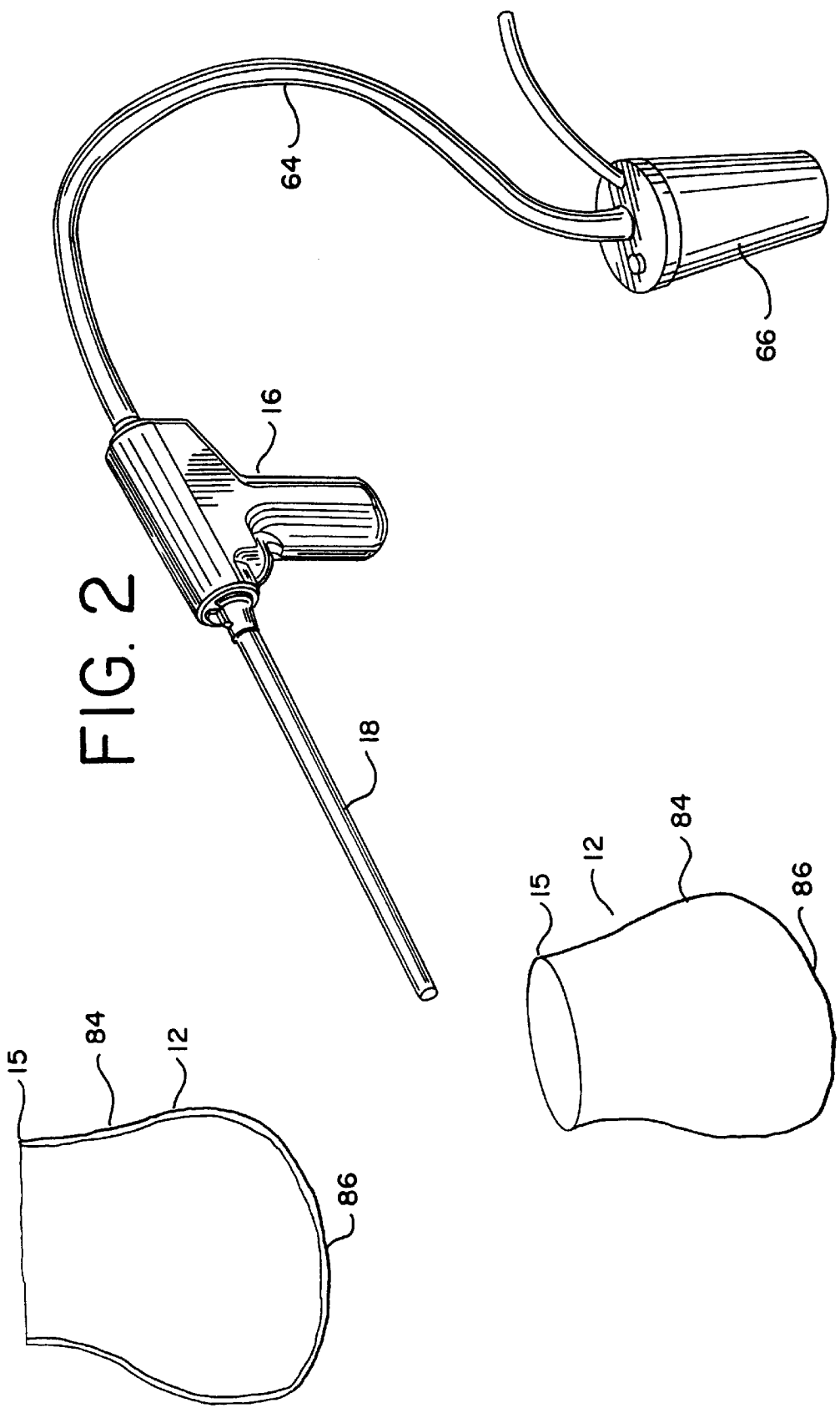

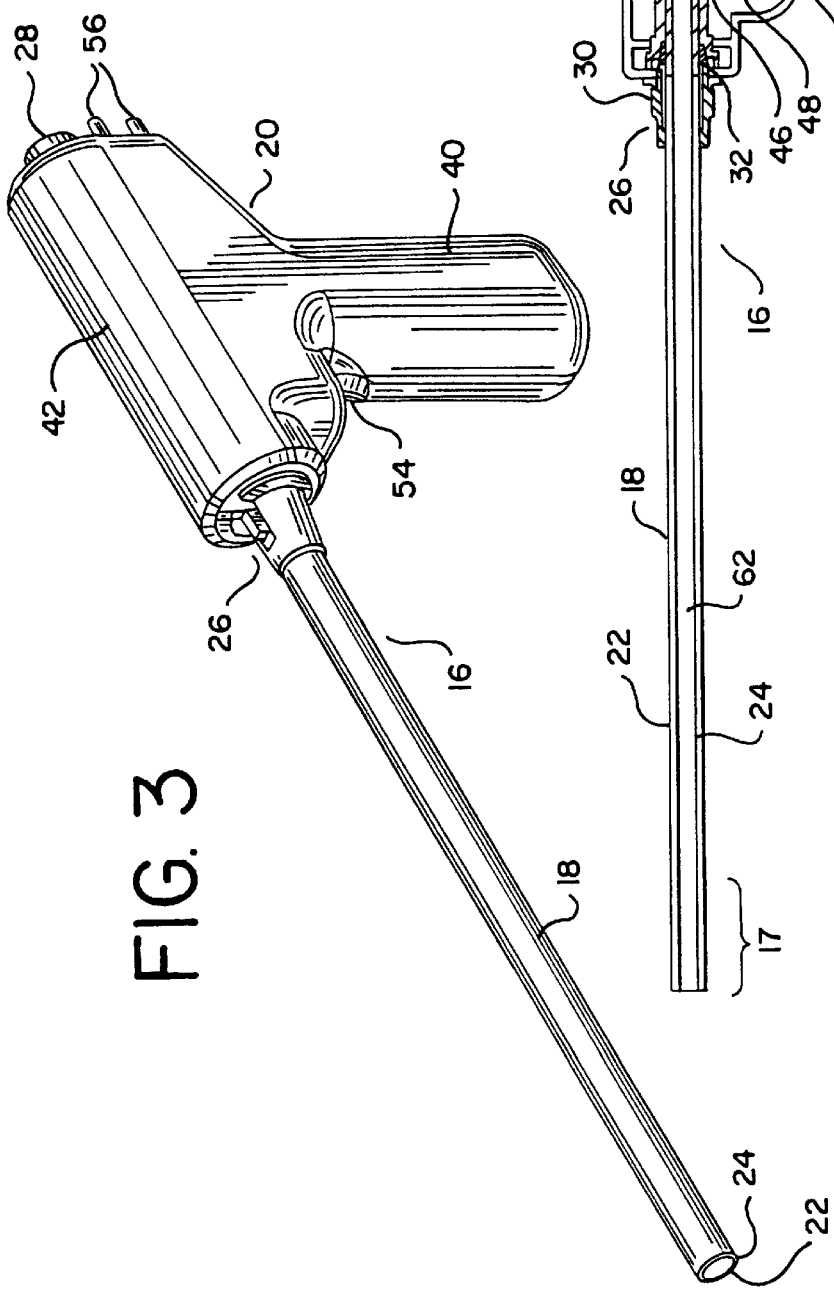

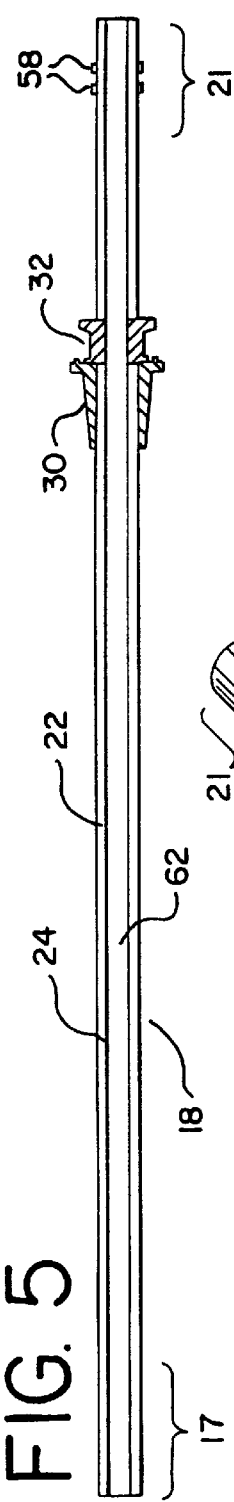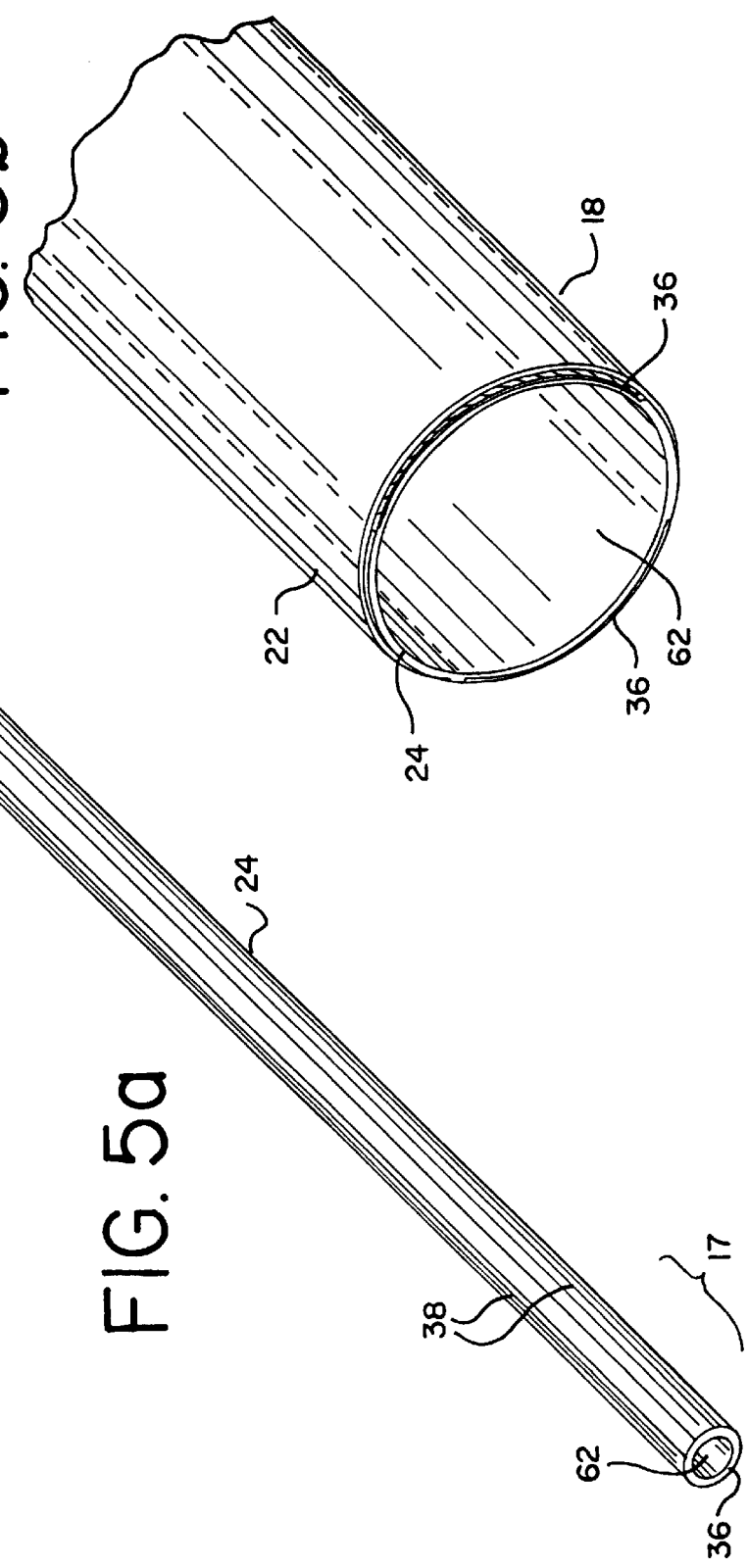

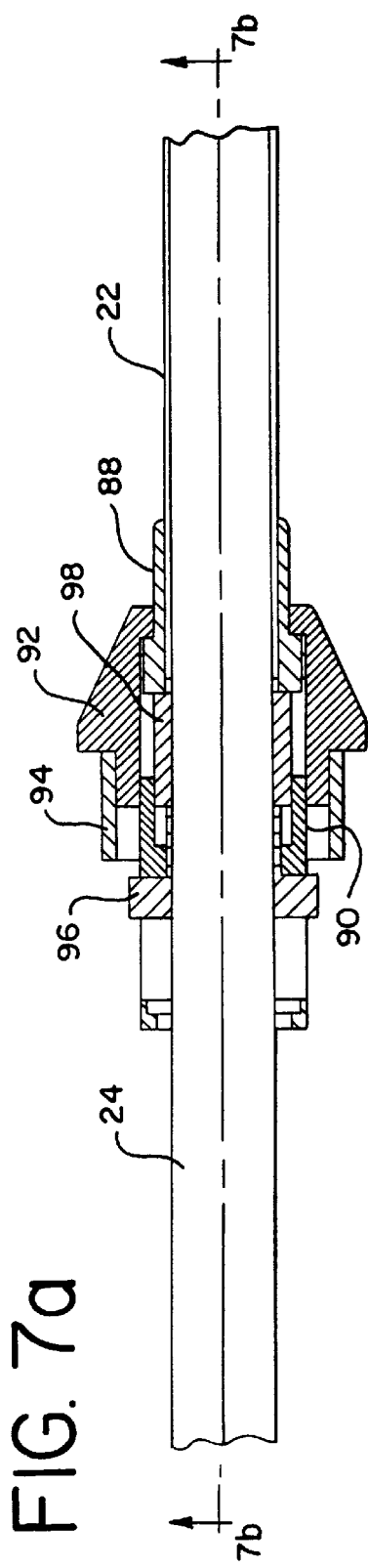
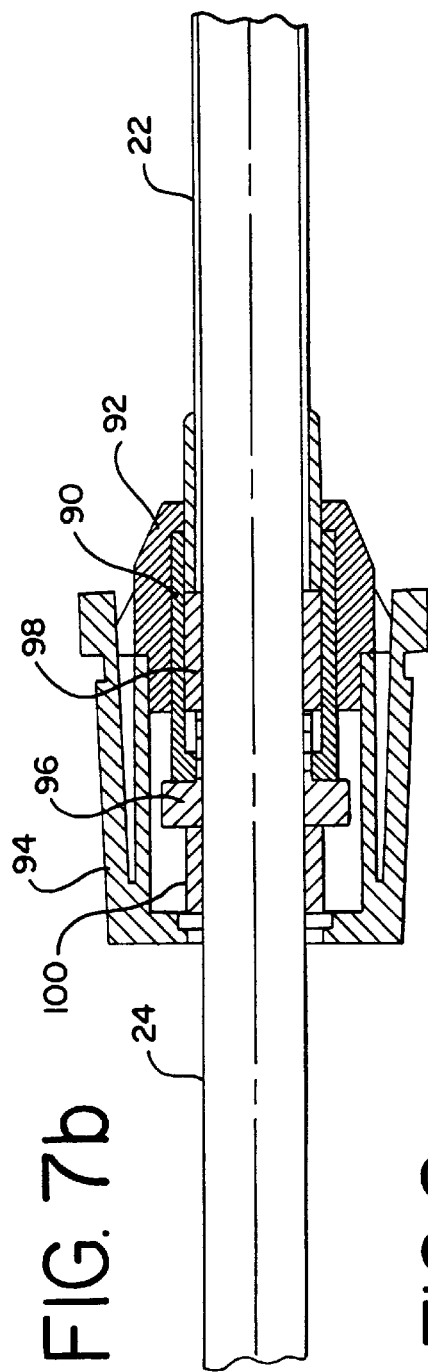
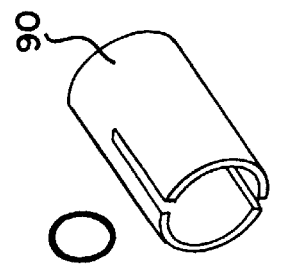
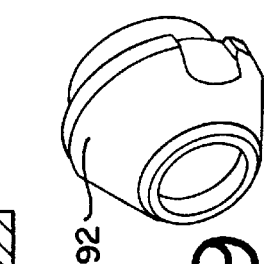
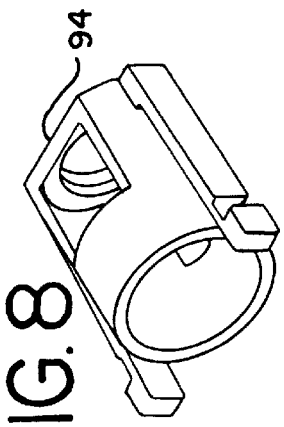

APPARATUS AND METHOD FOR MORSELATING AND REMOVING TISSUE FROM A PATIENT

CROSS REFERENCE TO RELATED APPLICATION

This application is a division of U.S. application Ser. No. 08/386,970, filed Feb. 10, 1995.

The present invention relates generally to apparatus and methods for removing tissue from the body of a human patient. More particularly, the present invention concerns novel apparatus and methods for morselating and removing body tissue through a relatively small incision in the patient.

BACKGROUND OF THE INVENTION

So-called minimally invasive surgery has become increasingly popular in a variety of surgical procedures. Minimally invasive surgery typically involves introducing surgical devices into a patient through small access incisions, in contrast to obtaining full and open access to the surgical site through large incisions.

Briefly, minimally invasive surgery is typically carried out through one or more relatively small incisions, which are usually between approximately ½ and 1½ inches in length, and through which an entry tube or trocar is placed. Optical and medical instruments are inserted through the trocar(s) to allow the physician to view the surgical area and to target the organ or tissue that is the subject of the surgery, and then to carry out the desired surgical procedure. Because of the relatively small diameter of the trocar(s), however, withdrawal of the target tissue therethrough can be difficult, particularly if the tissue is dense or muscular, such as a kidney, uterus or uterine myoma.

One previously accepted technique for removing such tissue required manually cutting the tissue into smaller pieces within the body cavity, which pieces were then removed through the trocar by graspers. This procedure, however, in addition to being very tedious and time consuming, also suffers from a number of other possible drawbacks, including possible excessive bleeding, possible accidental cutting of other tissue and possible contamination of the abdominal cavity with target tissue.

A morselation device is described in U.S. Pat. No. 5,290,303. That device uses an inner rotating tube and an outer stationary sheath, the inner tube extends beyond the sheath and has a tapered end for severing tissue. A further outer tube or shield may also be used over the sheath. This device may be used with a tissue bag, such as shown in U.S. Pat. No. 5,037,379. The tissue to be morselated may be placed in the bag and the device inserted into the bag to carry out the morselation within the pouch.

One of the concerns with the device shown in the '303 patent is possible puncture of the pouch by the rotating tube, with accompanying potential contamination of the anatomical space, as well the time consuming insertion and placement of a new pouch within the body cavity. Although the bag disclosed in the '379 patent has two layers, including a puncture resistant inner layer, the above-mentioned concern is still present. In addition, the multi-layer construction with a higher strength inner container may make folding and insertion of the pouch into the abdominal cavity more cumbersome.

More recently, in U.S. Pat. No. 5,304,124, an apparatus and method were disclosed for removing a uterine myoma. In that method, a tube is inserted through the trocar and into the myoma. A wire loop, which may energized by radio frequency energy, is located at the distal end of the tube to cauterize the tissue as the tube is inserted into the myoma, resulting in a core of tissue being located within the tube. A separate morselator is then inserted into the tube to cut up the tissue (such as by rotary blades, laser, or a rotary whip), and the morselated tissue is then evacuated. Although such a procedure may be an advance over a purely manual procedure, this procedure is still relatively complicated, requiring separate steps and apparatus to core and to morselate the tissue.

In addition, the procedure described in the '124 patent, when utilized with radio frequency ("RF") energy, uses a separate grounding or return electrode or antenna in contact with the skin of the patient, for example, that the patient lies on. As is well known in the art, such an application of RF energy has certain shortcomings. It requires the energy to travel between the electrodes, a relatively long distance through the body, with possible adverse effect on other body tissue. It also may result in accidental injury to non-target tissue, for example, if the active electrode is inadvertently brought into contact with non-target tissue. Also, this patent discloses a relatively complex mechanism to sever the tissue core from the myoma.

Accordingly, it is a general object of the present invention to provide apparatus and methods for removing target tissue through a trocar, which apparatus and method are more simplified and/or easier to use than the apparatus and method described above, and reduces the risk of accidental injury to non-target tissue.

GENERAL SUMMARY OF THE INVENTION

As set forth in the appended claims, the present invention is generally embodied in apparatus and methods for morselating and/or removing target tissue from the body cavity of a patient, such as through the relatively small incisions) that are typically used in minimally invasive surgical procedures.

More particularly, the present invention is generally embodied in a morselator, a tissue container for containing resected tissue to be morselated, and their methods of use. In general, the morselator of the present invention may comprise an elongated shaft having an inner tube and an outer tube extending between proximal and distal end portions. At least one of the tubes is rotatable and an electrode surface is carried by the rotatable tube(s) in proximity to the distal end thereof.

The foregoing apparatus may be used for removing tissue from within a body cavity of a patient by inserting the distal end through an incision in the patient, energizing and rotating the electrode and advancing the electrode into the resected tissue in order to morselate it. The morselated tissue is then removed through the lumen of the inner tube.

Preferably a second electrode of opposite polarity is used with the first mentioned electrode, with one of the terminals being a RF energy active electrode and the other being a RF energy return electrode, to morselate tissue therebetween. The additional electrode may be located, in one embodiment, at the distal end of the shaft or, when the morselator is used to morselate tissue within a resected tissue container, the additional electrode may be defined within the container, such as by a conductive inner surface of the container or by having the additional electrode otherwise disposed within the container.

In accordance with further aspects of the present invention, the combination of a resected tissue container and a morselator may be provided for morselating resected tissue within the body cavity of a patient. In such a combination, the tissue container is insertable through an incision into a body cavity of a patient. The container defines an interior chamber for containing the resected tissue. The morselator has a proximal end portion and a distal end portion. One electrode is carried on the distal end portion and is operable to assist in the morselation upon insertion through an incision and into the resected tissue container. A second electrode of opposite polarity also is disposed in the container. In this combination, the resected tissue container contains the resected tissue and helps protect surrounding tissue from inadvertent or undesirable contact with the electrodes or RF energy associated therewith.

In accordance with another aspect of the present invention, a tissue container is provided for containing resected tissue during morselation. The tissue container is comprised of a flexible wall which defines an inner chamber adapted to be received within a body cavity of a patient. The wall comprises a non-conductive outer surface and a conductive inner surface, which inner surface also may serve as an electrode of opposite polarity when only one type of electrode (e.g., active or return) is carried on the morselator.

The above is only a summary of the present invention in certain of its more general aspects. Accordingly, for a more complete understanding of these and other features and advantages of the present invention, reference should be made to the following detailed description.

BRIEF DESCRIPTION OF THE DRAWINGS

The present invention is set forth in greater detail in the following description of the attached drawings, of which:

FIG. 2 is an overall perspective representation of apparatus embodying the present invention and that may be used in practicing the method of the present invention, including a tissue container, hand-held morselator, and specimen collection jar.

FIG. 2a is a cross-sectional view of the tissue container of FIG. 2.

FIG. 3 is a perspective view of the morselator shown in FIGS. 1 and 2 and embodying the present invention.

FIG. 4 is a cross-sectional view of the apparatus of FIG. 3.

FIG. 5 is a cross-sectional view of a multiple-tube elongated shaft portion of the apparatus of FIGS. 3 and 4.

FIG. 5a is a perspective view of an inner tube of the multiple-tube shaft shown in FIG. 5.

FIG. 5b is a perspective view of the distal end of the multiple-tube elongated shaft shown in FIG. 5

FIG. 7a is a cross-sectional view of an elongated shaft for removable attachment as part of a morselator.

FIG. 7b is a cross-sectional view of the shaft of FIG. 7a taken along lines 7b—7b of FIG. 7a.

FIG. 8 is a perspective view of snap collar employed in the apparatus of FIGS. 7a–7b.

FIG. 9 is a perspective view of a main collar employed in the apparatus of FIGS. 7a–7b.

FIG. 10 is a perspective view of an outer tube guide employed in the apparatus of FIGS. 7a–7b.

DETAILED DESCRIPTION OF THE DRAWINGS

The present invention is particularly useful in morselating and removing tissue from a body cavity of a patient through relatively small incisions, such as those employed in so-called minimal invasive surgery.

An initial description of the method of use may aid in understanding the apparatus of the present invention. In minimally invasive surgery, one or more relatively small incisions 10 are normally made in the patient. As is well known in the art, particularly in abdominal surgery, these incisions are typically made by first inflating the abdominal cavity to raise the skin away from the underlying organs. The skin is then grasped, and a trocar, which may have a puncture tip, is inserted through the skin and peritoneal membrane 11 and into the abdominal cavity forming a relatively small access incision or opening through the skin. Surgical instruments, optical fiber devices, light sources and the like may then be inserted through the trocars to carry out the desired surgical procedure on whatever target tissue is involved. Although described generally in terms of abdominal surgery, the method and apparatus of the present invention are not limited to a specific type or location of surgery.

The method of the present invention is typically carried out after the surgery, such as that described above, has been carried out, and the target tissue has been resected. The target or resected tissue may be any organ, tumor, growth, or other tissue, although it is contemplated that the present invention is particularly useful for tissue that is especially dense or muscular, such as a uterus or kidney, and unsuited for simple withdrawal through a trocar, or for tissue that may be infectious or malignant. Similarly, the present invention is not limited to any particular technique or apparatus for the resection of the target tissue.

Figure 1:
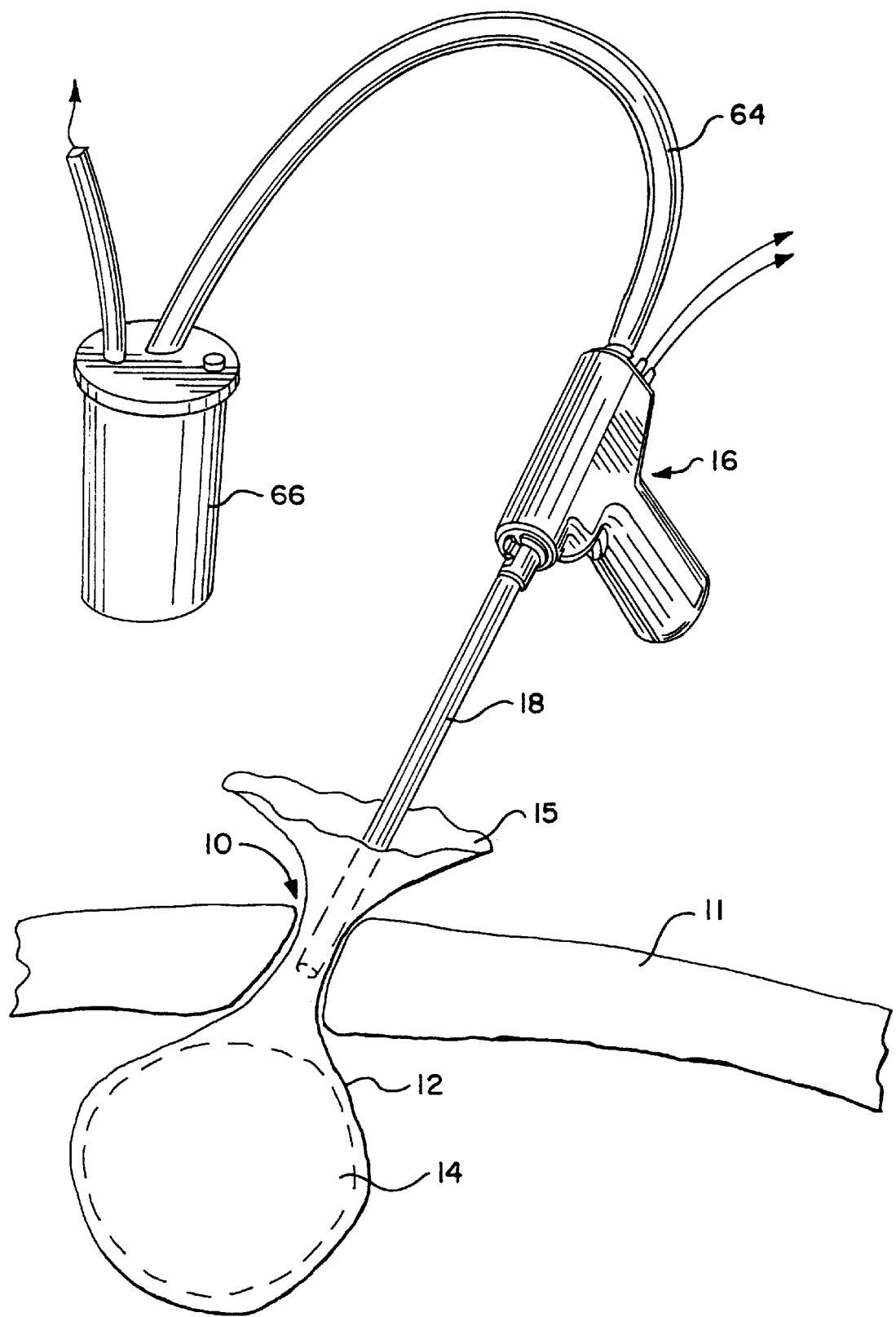
FIG. 1 is an overall perspective representation of the present invention, including morselator extending into a tissue container in a small incision in the body cavity of a patient.

Referring to FIGS. 1 and 2, in accordance with one aspect of the present invention, at least a portion of a tissue container such as a flexible bag or pouch 12, is inserted through the incision 10 and into the patient's body cavity. It is anticipated that in most procedures the entire bag or pouch 12 will initially be inserted into the body cavity by rolling or folding it and inserting it through the trocar located in the incision. The resected tissue 14 is then placed into the bag or pouch. The bag or pouch may be located entirely within body cavity or the lip or marginal edge 15 of the bag or pouch may then pulled through the incision, for example after removal of the trocar, to allow the bag or pouch to be held or gripped by the surgeon during the morselating.

Morselator 16 of the present invention is then inserted through incision 10 into the bag or pouch 12. When the bag or pouch has been inserted into the body cavity, and the lip 15 of the bag or pouch is withdrawn or pulled up through the small incision 10 and externalized, the distal end 17 of elongated shaft 18 of the morselator 16 is inserted through the lip or opening 15 of the bag or pouch 12 and through the incision to the resected tissue 14. A rotating electrode on the distal end of the shaft morselates the resected tissue by coring it or slicing it while it remains within the portion of the bag or pouch 12 that is within the body cavity. As used herein, morselating means cutting, coring, slicing, chopping or any other way of sub-dividing tissue into smaller pieces. The morselated tissue is then removed, such as by suction through the shaft.

Turning now to the illustrated morselator employed in and embodying the present invention, FIG. 3 is a perspective view of the preferred morselator 16 shown in FIGS. 1 and 2. For the purposes of this description and the claims, the morselator 16 may also be referred to generically as an "electrosurgical device".

As shown in FIG. 3, the morselator 16 includes, in addition to the elongated shaft 18, a hand piece 20 at the proximal end. 21 of the elongated shaft for gripping by the surgeon and for mounting the elongated shaft 18 and the controls for the morselator. Referring first to the elongated shaft, which is also shown in FIGS. 5–5b, the shaft is made up of a stationary outer tube 22 and an inner tube 24 rotatably received within the outer tube. The elongated shaft may be permanently attached to the hand piece, with the entire morselator being disposable or reusable. Alternatively, as discussed later, the elongated shaft may be disposable and removably attachable to a reusable hand piece.

As shown in FIGS. 4 and 5, the inner tube extends from the distal end 17 of the elongated shaft 18, through nose 26 of hand piece 20 and terminates in a proximal suction connection fitting 28 on the hand piece. The outer tube 22 extends from the distal end 17 of the shaft 18 to a proximal tube collar 30, which is fixedly attached to the nose of the hand piece.

The inner tube 24 has an inner tube collar 32 attached at the proximal end portion of the inner tube. The inner tube collar is received within and preferably keyed or otherwise attached in rotationally locked engagement with an inner body sleeve 34 mounted in the hand piece 20. A keyed arrangement between the inner tube collar and the inner body sleeve permits easy removal and disposal of the inner tube and reuse of the hand piece. Alternatively, the inner tube collar may be permanently attached or bonded to the inner body sleeve 34, and the entire morselator may be disposable or resterilizable.

Although not necessarily preferred, the inner tube 24 may be axially movable relative to the outer tube 22, and spring loaded, such as by a compressed spring (not shown) between inner tube collar and the nose 26, to bias the inner tube to a position where the distal end of the inner tube extends slightly beyond the distal end of the outer tube. As a result, when an axial force is exerted on the distal end of the inner tube, such as when it contacts the tissue container, the inner tube is forced back into the outer tube. This feature may prevent unnecessary damage to the electrodes at the distal end of the inner tube and to the tissue container.

The inner and outer tubes are preferably made of a substantially electrically non-conductive material, such as a fiber glass-epoxy composite or a polymer. Alternatively, the walls of the inner and outer tubes may have a metal core for strength and be coated with a substantially non-conductive or insulating material. The diameter and thickness of the inner and outer tubes may be selected depending on the desired procedure and/or target tissue involved. For morselating dense or muscular tissue, fiberglass epoxy inner and outer tube walls of approximately 0.007 inches thick have been found suitable. Because of their thinness, the tubes are shown simply as lines in FIGS. 4 and 5.

For morselating resected tissue, a pair of electrode surfaces 36 of opposite polarity are preferably provided at the distal end 17 of the shaft 18. In the illustrated embodiment, the electrode surfaces are provided at the distal end of thin conductive metal strips 38 that extend along and are bonded to the outer surface of inner tube 24. The distal ends of these strips, which provide the electrode surfaces, terminate in proximity to the distal ends of the inner and outer tubes, although they may extend slightly beyond the distal end of the inner and outer tubes, be recessed slightly between the inner and outer tubes, or terminate at the distal end and still function satisfactorily.

The conductive strips 38, such as aluminum or stainless steel strips or foil, may be placed on the tube wall by, for example, bonding the strips to the tube or manufacturing the tube in such a way that the strips 38 are located inside the wall of the tube, and the strips exposed at the distal end. The outer tube 22, which may be made completely of insulating material or have an interior surface of non-conductive material, insulates the electrical conductors on the inner tube from surrounding tissue, and the insulating material on the inner wall of the inner tube insulates the conductors from any tissue within the inner tube. ("Insulating" and "non-conducting" are used interchangeably in this description.)

The present invention, however, is not limited to the use of conductive strips to transmit electrical energy from the proximal to the distal end of the elongated shaft. Any type of conductor or conductive material can be used. Thin and relatively wide conductive strips are preferred, however, for delivering high power RF energy to the electrode surfaces because they allow a maximum amount of current to be carried along the length of the inner tube without unduly increasing the spacing between and/or wall thickness of the tubes. Thin conductors are also ideal for RF energy because the high frequency current travels primarily on the surface of a conductor, so a thin conductor with a large surface area, such as the thin strips 38 in FIG. 5a, offers what is believed to be the best possible combination of current carrying capability and minimal tube wall spacing and/or wall thickness. Further, the conductive strips conduct RF energy much more efficiently than a wire of the same cross-section since a thin strip conductor has a much larger surface area than a wire of the same cross-section.

Referring to the hand piece 20 of the morselator 16, shown in FIG. 3 and in vertical cross-section in FIG. 4, the hand piece 20 includes a lower handle portion 40 for the surgeon to grip and an upper body portion 42 to mount the elongated shaft 18. The hand piece also includes the controls for the morselator. The body portion 42 of the morselator includes a motor 44, which is preferably a lower power-consumption high torque motor such as the type commonly used in electric screwdrivers, for rotating the inner tube 24 of the elongated shaft 18. In order to rotate the inner tube, the motor 44 is connected to a drive gear 46 that mates with a driven gear 48 which is connected to the inner body sleeve 34.

As explained above, the inner body sleeve 34 is rotationally locked to the inner tube 24 through collar 32. Accordingly, when the motor 44 is engaged, it causes the inner body sleeve 34 and inner tube 24 to rotate. In the preferred embodiment, only the inner tube rotates. It is within the scope of this invention, however, for the outer tube to rotate, and the inner tube to remain stationary or for both tubes to rotate.

The handle portion 40 of the hand piece 40 of the morselator 16 not only includes a grip 50 for the surgeon to hold while using the morselator, but also may include a battery pack 52 and a switch or trigger 54 to turn the morselator on and off. The battery pack 52 may be rechargeable for a reusable handle or a one-time use battery for a disposable handle. To turn the morselator on and off, the battery pack 52 is electrically coupled to the motor 44 via the switch 541 which is preferably in the form of a trigger.

The switch 54 also serves to the couple RF contacts 56 to tube contacts 58 on the inner body sleeve 34. Tube contacts 58 are in the form of spaced-apart rings. Each ring is in electrical contact through the inner body sleeve, with one of the conductor strips on the inner tube. Brushes or sliding contacts 60 are in direct contact with the rings. One of the brushes is directly coupled to one of the RF contacts. The other brush is coupled to the other RF contact through a circuit controlled by switch 54.

Therefore, when the switch 54 is turned on or the trigger is depressed, it completes the circuit from the battery pack 54 to the motor 44 and activates the motor 44, which causes the gear assembly to turn, and, the inner body sleeve 34 and the inner tube 24 to rotate. Additionally, when the switch is turned on or the trigger depressed, it completes the circuit between at least one of the RF contacts 56 and the tube contacts 58, allowing RF electrical energy to flow from the RF contacts 56 to the conductors (see e.g. FIG. 5*a*) located on the surface of the inner tube 24, and to the electrode surfaces 36 at the distal end of the morselator 16.

Preferably, morselated tissue is removed through the morselator 16 via an inner tube lumen 62 extending between the distal 17 and proximal 21 ends of the morselator. A suction source or apparatus (not shown) may be used to suction the tissue and remove it from the body cavity. More specifically, the suction apparatus is coupled to connection fitting or tube 28, which communicates with proximal end 21 of the inner tube 24 of the morselator 16, and is used to suction the morselated tissue therethrough. The suction apparatus may include a suction tube 64 coupled to a specimen collection canister 66, which is then coupled to the suction source. The suction may be manually controlled by the surgeon, or the morselator 16 also could include a suction control (not shown), such as a rocker switch or similar mechanism, to allow the suction control to operate at the same time or in tired relation with the motor and/or RF energy activation. Alternately, other devices such as a grasping instrument or a myoma screw could be used to pull the morselated tissue up through the inner tube of the morselator while the tissue is being morselated.

The morselator of the present invention preferably uses an RF energy source of the type well known in the field. As commonly known in the field, such a radio frequency energy source may provide high voltage electrical current at a frequency between 100 KHz and 1 MHZ. The energy source can use either an RF monopolar or a bipolar RF energy source. In the present invention, however, because of the small surface area (the end edge of strip 38, for example) of the electrodes it is particularly desirable to use RF monopolar power source, with one of the electrodes connected to the monopolar terminal of a typical RF energy power supply and the other electrode attached to the return.

For morselating tissue there are various configurations of electrodes, as shown in FIGS. 5*b* and 6*a*–6*g*, that can be used in the present invention. It is understood that these are merely examples of different configurations and that other configurations, modifications, and variations would be readily apparent to one skilled in the art and are intended to be included within this application. In each configuration shown in FIGS. 5*b* and 6*a*–6*g*, at least one electrode is active and can be electrically coupled to a source of electrical energy, such as for example a RF monopolar current source, via one of the RF contacts 56 and a conductor such as conductive strip 38. One or more of the other electrodes is electrically coupled to a ground/return circuit, such as a monopolar ground return, via the other RF contact 56. Alternatively, bipolar energy could be used.

Figure 6A:
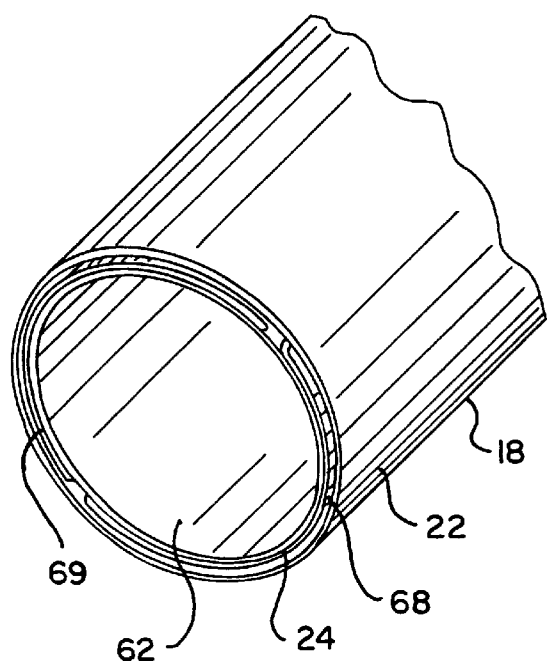
FIGS. 6a–6g are perspective views of different configurations of the distal end of the multiple-tube elongated shaft shown in FIG. 5.
Figure 6B:
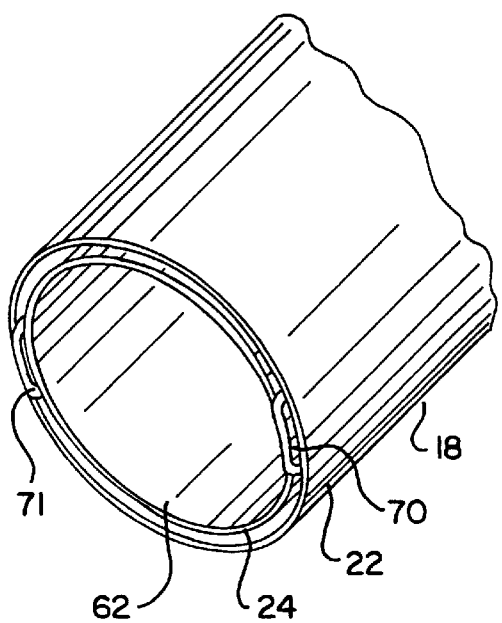
Figure 6C:
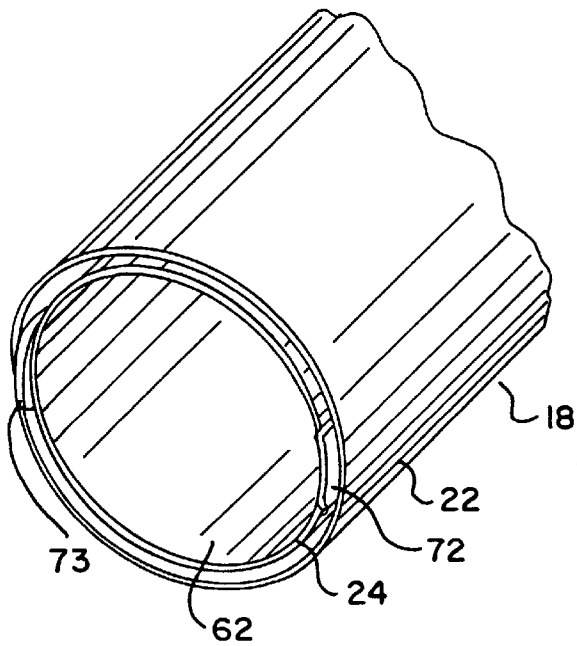
Figure 6D:
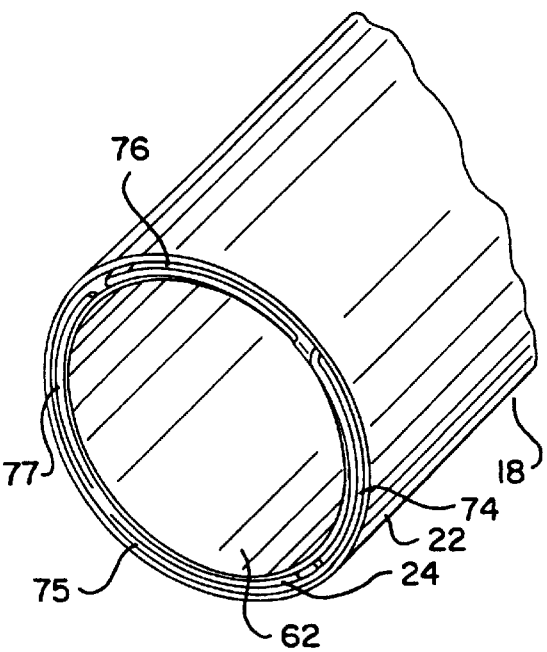

FIGS. 6*a*–6*d* show the distal end 17 of the elongated shaft 18 wherein, both electrodes are located between the inner tube 24 and the outer tube 22 and can be carried by the inner tube 24. FIG. 6*a* shows two arcuate or half-circle type electrodes 68, 69. These electrodes may be, for example, wires or strips. One electrode would be electrically coupled to ground/return, and the other would be electrically coupled to a monopolar active current. The embodiment shown in FIG. 6*b* utilizes a different configuration with wire electrodes 70, 71 on the outside of the inner tube 24. These electrodes may be in the shape of wire loops. The wires extend slightly beyond the distal end of the inner tube. As a result, the inner tube 24 may be recessed slightly in relation to the outer tube 22 with the ends of the wires 70, 71 just flush with the end of the outer tube 22. As in the embodiment in FIG. 6*a*, one electrode would be electrically coupled to ground/return, and one would be electrically coupled to a monopolar active current. In the embodiment in FIG. 6*c*, solid metal portions or strips 72, 73 are used instead of wires. These metal portions may be located on opposite sides of the inner tube and extend beyond the distal end of the shaft, and may also be electrically coupled to ground/return and a monopolar active current, respectively. In the embodiment shown in FIG. 6*d*, there are four electrodes 74, 75, 76, 77 wherein two electrodes 74, 77 would be electrically coupled to ground/return, and two electrodes 75, 76 electrically coupled to a monopolar active current.

Figure 6E:
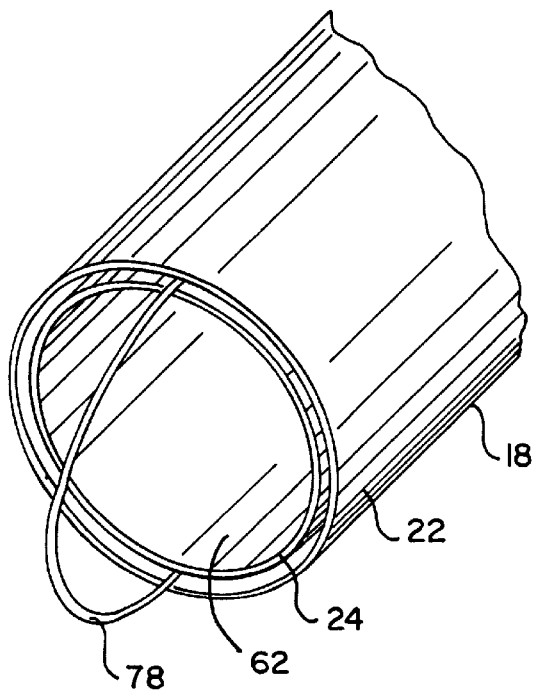
Figure 6F:
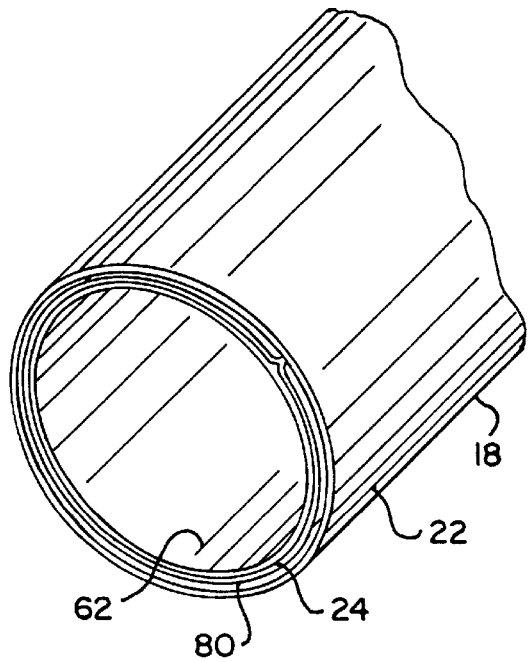
Figure 6G:
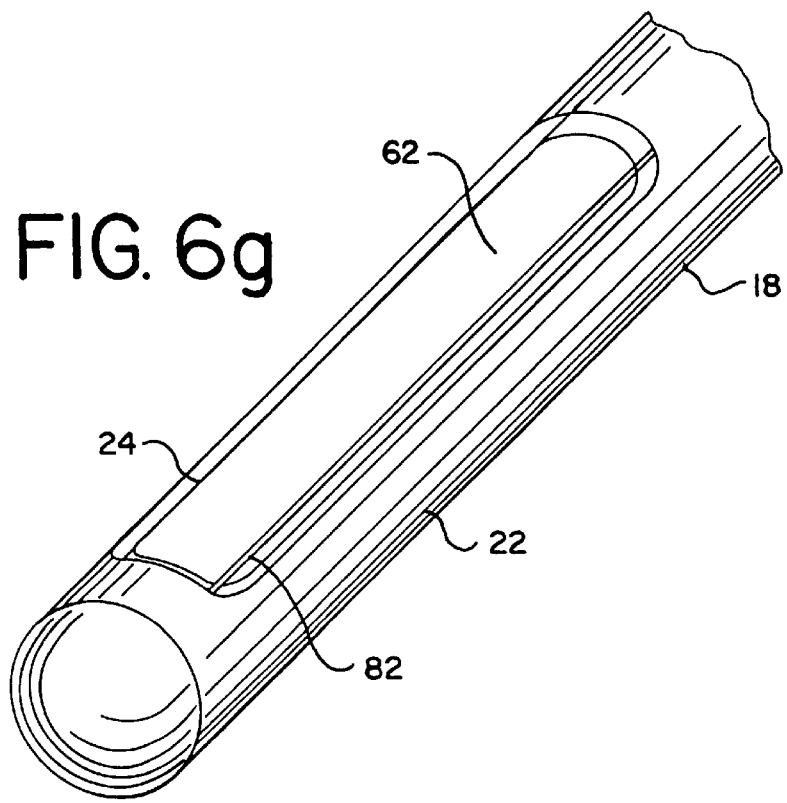

In the embodiment shown in FIGS. 6*e* and 6*f*, a different configuration is shown where one electrode is located between the inner tube 24 and the outer tube 22 while the end surface and/or outer surface of the outer tube 22 functions as the other electrode. Specifically, FIG. 6*e* shows a scoop type wire 75 which could be electrically coupled to a monopolar active current. The outer surface of the outer tube 22 is covered with a conductive material and acts as the other electrode, which can be electrically coupled to ground/return. In the embodiment shown in FIG. 6*f*, a single electrode 80, which may be a wire, strip, or simply the exposed end of a conductive tube, extends around the distal end of the inner tube and may be electrically coupled to a monopolar active current, with the ground/return electrode being the outer surface of the outer tube 22.

It may be necessary in some instances to have a portion of the side of the elongated shaft adjacent to the tissue to be removed. In those circumstances, the tissue can be shaved using the embodiment shown in FIG. 6*g*. In this embodiment, the inner and outer tubes 24, 22 are slotted at a distal side port, and a wire or strip electrode 82 extends the length of the side port and may be electrically coupled to a monopolar active current and function as a cutting edge as the inner tube 24 rotates inside the outer tube 22 to shave any tissue within the cutout portion of the tubes. Again, the edge surface or outer surface of the outer tube 22 is conductive and may be electrically coupled to ground/return. In all of these electrode configurations, the outer tube 22 may be covered with a conductive coating and used to provide a ground/return path.

Alternatively, the elongated shaft may be a single rotatable tube with a pair of electrodes of opposite polarity at the distal end. For example, a solid metal tube could be employed with an electrode of selected polarity carried at the distal end and a conductor extending along the length of the tube between the proximal end and the electrode at the distal end portions. Of course, to avoid short circuiting, the conductor would need to be insulated from the metal tube. In this alternative, the distal end of the metal tube itself could act as the other electrode of opposite polarity, and the tube body would function as the conductor between the proximal and distal end portions. In a single tube arrangement, various other combinations of conductive and non-conductive materials also could be used, such as a tube wall of non-conductive material with a pair of electrodes at the distal end and a pair of conductors extending along the tube body. Also, the wall of the tube could have three layers with non-conductive inner and outer surfaces and a metal core therebetween with the distal end of the metal core forming the other electrode and the core itself being a conductor.

Turning now to a more detailed description of the tissue container that may be used in accordance with the present invention, the container may be of various shapes, sizes or materials without departing from the present invention. As noted above, however, the tissue container is preferably in the form of a flexible bag or pouch 12. The bag or pouch 12 generally has side wall 84, bottom wall 86, and marginal edge or lip 15 defining the opening into the bag or pouch. The walls of the bag or pouch are preferably sufficiently flexible to allow the bag or pouch to be flattened or folded or rolled for insertion through a trocar or a relatively small incision into the body cavity.

In use in the preferred embodiment, the tissue is morselated by the rotating action of the inner tube and electrode and by pushing the distal end of the shaft against the bottom of the tissue container to sever the morselated tissue from the remainder of the resected tissue. Accordingly, the tissue container should be mechanically strong enough to withstand the force and abrasion caused by a morselator, as well as the local heating caused by electrodes. For this reason, it is preferred that the walls of the vessel be made as thick as possible, yet not so thick that the vessel cannot be folded or rolled up to fit through a trocar.

To insulate and protect surrounding tissue, the walls of the pouch or bag should be of a substantially non-conductive or electrically insulating material. High thermal resistance silicone rubber or fabric reinforced silicone rubber in the range of 0.010–0.015 inches thickness has the desired characteristics of flexibility, strength and non-conductivity, and is the preferred material. It is expected, however, that other materials may also be suitable and the present invention, in its broader respects, is not limited to a particular material for the tissue container.

As described briefly above, the preferred morselator may have both active and ground electrodes located on the shaft. Alternatively, only one electrode may be located on the shaft and the cooperating electrode be in the form of conductive surface on the inside of the tissue container. For the latter application, the tissue container preferably has a non-conductive outer surface, such as silicone, and a conductive inner surface such as a flexible metallic film or foil, such as aluminum or stainless steel foil. With proper attachment, the conductive inner surface can act as the ground/return electrode for RF energy application.

Alternatively, the tissue container may contain a separate conductor or an electrode there within, such as a wire or strip electrode of opposite polarity, to assist in morselating the resected tissue. The separate electrode could also be electrically coupled to active or ground/return and operate in conjunction with the electrode on the morselator for creating the needed cutting action.

As described briefly above, the inner and outer tubes 24 and 22 forming the elongated shaft may be removably attachable to the hand piece for disposability. FIGS. 7a–7b and 8–10 depict aspects of a snap-lock arrangement for removable inner and outer tubes. In FIG. 7a, outer tube 22 is attached or bonded to an outer tube collar 88. One end of outer tube collar 88 is received within outer tube guide 90, which is bonded to main collar 92, which is bonded to snap collar 94. Inner tube collar 96 is bonded to the inner tube 24 and held in spaced relationship from the outer tube collar by outer tube spacer 98 and from the snap collar by inner tube spacer 100. This construction allows the inner tube to rotate relative to the outer tube and both tubes to be snapped into a receiving nose collar that interfits with spring arms 102 of the snap collar. In such an embodiment, the inner tube could be rotationally locked to inner tube sleeve by a keyed fitting, such as a mating spline and groove or the like. Electrical contact with the contacts on the tube sleeve could be achieved by slidable spring contacts. Also, outer tube spacer 98 and/or inner tube spacer 100 could be in the form of a spring to allow relative axial movement between the inner and outer tubes.

The features and method of the present invention have been described in connection with the accompanying drawings for the purposes of illustration and not limitation. It is intended that this application include those modifications, variations and additions that would be readily apparent to one of ordinary skill upon reading this description. Accordingly, for ascertaining the scope of the present invention, reference must be made to the appended claims.

What is claimed is:

1. A method for removing tissue from within a body cavity of a patient through an incision in the patient comprising:

providing a morselating apparatus comprising an elongated shaft having proximal and distal end portions, the elongated shaft being rotatable and having a lumen extending between the proximal and distal end portions with a first electrode being carried on the distal end of the elongated shaft;

providing a second electrode;

inserting through an incision in the patient the distal end of the elongated shaft and the second electrode;

contacting the tissue to be removed with the second electrode;

energizing the first electrode by electrically coupling the electrode to a source of radio frequency energy;

rotating said elongated shaft and the electrode;

engaging the tissue to be removed with the energized rotating electrode to morselate the tissue; and removing the morselated tissue through the lumen of the elongated shaft.

2. The method of claim 1 wherein the first electrode is an active electrode.

3. The method of claim 2 wherein the elongated shaft includes the second electrode at the distal end portion thereof and wherein the second electrode is a return electrode.

4. The method of claim 3 wherein said elongated shaft comprises an outer tube and an inner tube disposed within the outer tube and the electrodes are both carried on the distal end of the inner tube.

5. The method of claim 1 wherein the step of removing includes suctioning the morselated tissue through the lumen of the elongated shaft.

6. The method of claim 1 wherein the morselating and removing steps occur simultaneously.

7. The method of claim 1 further including:

providing a resected tissue container;

inserting the resected tissue container through an incision in the patient and placing the resected into the container before inserting the elongated shaft;

inserting the distal end of the elongated shaft into the container; and carrying out the energizing, rotating advancing and removing steps inside the container.

8. The method of claim 7 wherein the tissue container has an inside surface that is non-conductive, and wherein the elongated shaft includes an additional electrode at the distal end thereof and wherein one of the electrode is an active electrode and the other of the electrodes is a return.

9. The method of claim 7 wherein the tissue container has an inside surface that is conductive and defines an electrode of opposite polarity to the electrode carried by the shaft.

10. The method of claim 7 wherein the tissue container has an inside surface that is conductive and defines a monopolar return electrode, and the electrode carried by the shaft comprises a monopolar active electrode.

11. The method of claim 7 wherein the inside surface of the container is silicone.

12. The method of claim 11 including pressing the distal end of the shaft against the inside surface of the container after advancing it into the tissue to fully sever the morselated tissue.

13. A method for removing resected tissue from within a body cavity of a patient through an incision in the patient comprising:

inserting a resected tissue container through an incision in the patient and placing the resected tissue into the container;

inserting through the incision in the patient and into the container the distal end of an elongated shaft being rotatable and having a lumen extending between the proximal and distal end portions;

energizing an electrode carried on the distal end of said elongated shaft by electrically coupling the electrode to a source of radio frequency energy;

rotating said elongated shaft and the electrode;

engaging the tissue to be removed with the energized rotating electrode to morselate the tissue; and removing the morselated tissue through the lumen of the elongated shaft.

14. A method for removing resected tissue from within a body cavity of a patient through an incision in the patient comprising:

inserting through the incision in the patient the distal end of a rotatable elongated shaft having a first electrode at its distal end and having a lumen extending between the proximal and distal end portions;

contacting the resected tissue with a second electrode remote from said elongated shaft;

energizing said electrodes by electrically coupling said electrodes to a source of radio frequency energy;

rotating said elongated shaft and the electrode;

engaging the tissue to be removed with the energized rotating electrode to morselate the tissue; and removing the morselated tissue through the lumen of the elongated shaft.

* * * * *